(12) United States Patent
Speiser et al.

(10) Patent No.: US 8,858,233 B2
(45) Date of Patent: Oct. 14, 2014

(54) SIMULATION SYSTEM FOR TRAINING IN ENDOSCOPIC PROCEDURES

(75) Inventors: Bjoern Speiser, Rottweil (DE); Bernhard Gloeggler, Tuttlingen (DE); Thomas Hinding, Aldingen (DE)

(73) Assignee: Karl Storz GmbH & Co. KG (DE)

( * ) Notice: Subject to any disclaimer, the term of this patent is extended or adjusted under 35 U.S.C. 154(b) by 253 days.

(21) Appl. No.: 12/897,385

(22) Filed: Oct. 4, 2010

(65) Prior Publication Data
US 2011/0086332 A1 Apr. 14, 2011

(30) Foreign Application Priority Data
Oct. 9, 2009 (DE) .......................... 10 2009 048 994

(51) Int. Cl.
*G09B 23/28* (2006.01)

(52) U.S. Cl.
CPC ................................... *G09B 23/285* (2013.01)
USPC ............ 434/219; 434/262; 434/266; 434/267

(58) Field of Classification Search
CPC ...................................................... G09B 9/00
USPC .................................. 434/262, 266, 267, 219
See application file for complete search history.

(56) References Cited

U.S. PATENT DOCUMENTS

| | | | |
|---|---|---|---|
| 7,249,951 B2 * | 7/2007 | Bevirt et al. | 434/262 |
| 7,824,329 B2 * | 11/2010 | Aizenfeld et al. | 600/158 |
| 2005/0018885 A1 * | 1/2005 | Chen et al. | 382/128 |
| 2005/0033117 A1 * | 2/2005 | Ozaki et al. | 600/109 |
| 2005/0196739 A1 | 9/2005 | Moriyama | |
| 2005/0196740 A1 * | 9/2005 | Moriyama | 434/262 |
| 2005/0217727 A1 | 10/2005 | Uesugi et al. | |
| 2005/0245789 A1 * | 11/2005 | Smith et al. | 600/159 |
| 2006/0073458 A1 * | 4/2006 | Ehrhardt et al. | 434/262 |
| 2006/0234195 A1 * | 10/2006 | Grund-Pedersen et al. | 434/262 |
| 2007/0238929 A1 * | 10/2007 | Aizenfeld et al. | 600/158 |
| 2008/0286735 A1 * | 11/2008 | Cusano | 434/267 |

FOREIGN PATENT DOCUMENTS

| | | |
|---|---|---|
| DE | 102004046038 A1 | 4/2006 |
| EP | 1640940 A2 | 3/2006 |
| WO | WO 2007009763 A2 * | 1/2007 |

OTHER PUBLICATIONS

Endoscope Water Air Valve/button, Endoscope Water Air Valve/button Suppliers & Manufacturers on, Alibaba.com, <http://www.alibaba.com/endoscope-water-air-valve%252fbutton-suppliers.html>.*

* cited by examiner

*Primary Examiner* — Sam Yao
*Assistant Examiner* — Thomas Hong
(74) *Attorney, Agent, or Firm* — St. Onge Steward Johnston & Reens LLC

(57) ABSTRACT

A simulation system for training in endoscopic procedures includes an endoscope apparatus, which includes an operating part with at least one valve, a control device to generate a virtual image of an endoscopic operating scene depending on an actuation of the valve and a display device to display the virtual image, the endoscope apparatus includes for example a siphoning line, an insufflation line and/or a flushing line upon which the valve acts. The simulation system includes pressure-generating means to impact the siphoning line, the insufflation line and/or the flushing line with reduced or excess pressure, sensor means to measure pressure and/or flow in the siphoning line, the insufflation line and/or the flushing line and transmission means to transmit the measured values provided by the sensor means to the control device to be used in generating the virtual image.

19 Claims, 3 Drawing Sheets

SIMULATION SYSTEM FOR TRAINING IN ENDOSCOPIC PROCEDURES

CROSS-REFERENCE TO RELATED APPLICATIONS

The present application claims priority of German patent application No. 10 2009 048 994.0 filed on Oct. 9, 2009.

FIELD OF THE INVENTION

The present invention relates to a simulation system for training in endoscopic procedures as well as a method for training in endoscopic procedures.

BACKGROUND OF THE INVENTION

Apparatuses and methods of the aforementioned type are known in the art. For instance, patent application DE 10 2004 046 038 A1 discloses a virtual operating room simulator, which is intended in particular for training in endourological interventions. Contrary to surgical or endoscopic training models which make use of an actual reconstruction of a body part or of an internal body cavity, into which the point of an endoscope is inserted, to simulate a surgical or minimally invasive procedure, with a virtual simulator using "virtual reality" methods and computer support an image of a virtual environment, in particular of a body cavity, is generated interactively with user influence. According to DE 10 2004 046 038 A1, the virtual operating room simulator includes a simulation digital unit to generate such a virtual endoscopic image in real time, an instrument whose proximal part (that is, closer to the user) is copied from that of an endoscopically insertable instrument, and an instrument input unit to record the instrument. In addition to the display of the virtual image, the force reaction on the instrument or on a resection loop positioned distally (that is, remote from the user) is computed and communicated to the user. The instrument that is to be inserted into the instrument input unit and copied from a resectoscope comprises a feeder line and a run-off line for flushing liquid. Stopcocks are provided in each of the lines to allow opening and closing of the lines. Associated with these stopcocks are micropotentiometers that help to record the movement of the stopcocks. The corresponding signals are transmitted to the simulation processor unit and evaluated there to compute the virtual image.

Disclosed in US 2005/0196739 A1 is an endoscopic simulation system that includes a training endoscope especially adapted for simulation as well as a detector that records the movements of the distal end of a flexible shaft of the training endoscope controlled by the user, an image recording apparatus that registers the shape of a patient's internal hollow organ, and an image processor that generates a virtual three-dimensional image of the hollow organ from the recorded data. The operating portion of the training endoscope provides pushbuttons for air or for water flushing as well as for siphoning. On actuation of the particular pushbuttons, their movements are recorded and conveyed to the processor via an electric line.

Recording the movement of the stopcocks for air, water, and or siphoning and conversion into signals that can be evaluated by the image processor requires the integration of electronic or electrical elements into the training endoscope. With a flexible endoscope the actuation elements for air, water and siphoning are usually located in the handle. However, practically no space is available there for the related mechanical and electronic components. It must be kept in mind here that for a realistic simulation the handle of the training endoscope should correspond as closely as possible to that of the original endoscope in terms of size, shape and weight. Therefore it is very complex structurally to integrate appropriate sensors into the handle of the training endoscope. This is even more the case when an original endoscope appropriate for surgical procedures is to be adapted for use in such a simulator.

To ensure training conditions that are as realistic as possible, it is also essential to bear in mind, when using a training endoscope or a corresponding conversion of an original endoscope, that for the user the changes from the endoscope used clinically should be as few as possible in terms of the type and effect of the valve actuation, the force to be exerted for this, and the palpable reaction of the valve pushbuttons. Even this cannot be achieved to the desired extent, or is possible only at great effort, when sensors are to be integrated into the training endoscope to record the movement of the valve pushbuttons.

With many endoscopes, in particular flexible endoscopes, for controlling the three functions of siphoning, insufflating and flushing there are only two valve pushbuttons available to act on the corresponding lines, which run from a proximally mounted connection to the corresponding pumps through the handle all the way to the distal end section of the endoscope. By depressing a first valve pushbutton, a first valve is actuated that acts on the siphoning line by producing, or completely or partially interrupting, a connection between a siphoning pump that is connected to a proximal part of the siphoning line and a distal part of the siphoning line positioned distally from the valve. Accordingly, by depressing a second valve pushbutton a second valve is actuated that produces, or completely or partially interrupts, a connection between a flushing liquid reservoir, which is impacted with pressure by a flushing pump and is connected to a proximal part of the flushing line, and a distal part of the flushing line mounted distally from the valve. The second valve also comprises an aperture that is connected with the proximal and distal parts of the insufflation line. Connected with the proximal part of the insufflation line is an insufflation pump that produces an insufflation gas, such as air, at an appropriate excess pressure. As long as the aperture is open the insufflation gas can escape through the aperture so that no substantially increased pressure can build up in the insufflation line. In order to introduce gas via the distal part of the insufflation line into a body cavity into which the distal end of the endoscope is inserted, the user closes the aperture with one finger. Now pressure can build up in the insufflation line and the gas delivered by the insufflation pump is conveyed into the distal part of the insufflation line and from there into the body cavity. By simultaneously closing the aperture and partially depressing the second valve pushbutton, it is possible to insufflate and flush at the same time. In this manner the three functions, siphoning, insufflating and flushing, can be controlled with the help of two valve pushbuttons.

For a realistic simulation, the depressing of the valve pushbuttons must be detected and evaluated, as must the closing of the aperture in the second valve pushbutton. While the movement of the valve pushbuttons can be detected on depressing, for example by switches or potentiometers, recognition of the closing of the aperture requires a sensor that detects the presence of the finger that is closing the aperture. For this purpose it is possible in theory to employ a reflecting light barrier, but in this manner it is not possible to distinguish a complete closing of the aperture from an incomplete closing. Realistic training in operating the valves is therefore scarcely possible in the described arrangement of valves.

SUMMARY OF THE INVENTION

It is the object of the present invention to provide a simulation system for training in endoscopic procedures as well as a method for training in endoscopic procedures, such that the aforementioned disadvantages are avoided.

This object is achieved through a simulation system and a method as described and claimed herein.

An inventive simulation system includes an endoscope apparatus that comprises an operating part with at least one valve. The at least one valve acts on at least one line, which in particular can be a siphoning line, an insufflation line and/or a flushing line. The at least one valve can be actuated in particular by a user, preferably manually. It is also possible to provide an automatic or indirect actuation, for example a motorized actuation and/or one that is conveyed by mechanical, electric and/or electronic means, for example by a foot pedal or else by voice command. In a preferred embodiment the simulation system comprises a number of valves, particularly manually actuated valves, which act on a number of lines, in particular a siphoning line, an insufflation line and a flushing line. In preferred manner the endoscope apparatus corresponds to a proximal part of a clinically used endoscope or is placed downstream from it and comprises in particular a handle that contains the valve pushbuttons that are present in a clinically usable endoscope as is customary with such an endoscope and that serve to actuate these associated valves that act upon a siphoning line, an insufflation line and a flushing line.

In addition the simulation system comprises pressure-generating means that are positioned to impact the at least one line with reduced pressure or excess pressure, preferably with air at reduced or excess pressure. In particular, the pressure-generating means can each be connected with a proximal end of a siphoning line, an insufflation line and a flushing line. In so doing, various pressures can be generated in each case in the siphoning line, in the insufflation line and in the flushing line, said lines being preferably independent of one another so that the closing or opening of one of the lines causes no substantial pressure change in the two other lines.

According to the invention sensor means are provided to measure pressure and/or flow in the at least one line. Hereby the particular measured variable in the respective line is determined by at least one sensor in each case. Consequently, in particular, the pressure or flow in a siphoning line, in an insufflation line and in a flushing line can each be measured independently of one another.

In addition, transmission means are present to transmit the measured figures produced by the sensor means to a control device that evaluates the measured figures in the generation of a virtual image that in particular depicts an endoscopic view of an internal body cavity into which the distal end of an endoscope has been inserted. In particular, the control device includes at least one processor to execute the calculation operations required for this purpose, although a number of additional data and parameters can be used. Thus, for example, a storage device can be present to store data concerning the internal body cavity in which a surgical procedure is to take place for which training is to be conducted with the simulation system. Said data can be entirely or partly patient-specific and can also include data on the access route, so that insertion of the distal part of the endoscope into the internal body cavity can also be simulated. In addition other parameters of the endoscope can be processed which for instance can depict, for example, the degree of insertion of the endoscope shaft into the cavity, the curvature of the shaft, the angle of the distal end that can be controlled by the user, the actuation of an endoscopic working instrument that is inserted by the endoscope shaft, and the like. Methods for generating such a virtual image are known per se under the term "virtual reality," as are computer systems to execute such methods; we refer in particular to the aforementioned patent application DE 10 2004 046 038 A1.

The image generated by the control device, here designated as "virtual image," depicts the scene that would be recorded in executing the corresponding endoscopic operation with the help of the optic systems found in the endoscope and of a video camera associated with the endoscope and would be displayed for a user, in particular for the physician conducting the surgical operation. For this purpose the simulation system includes a display device to display the virtual image generated by the control device, for example a video screen, a video projector or a display device positioned on the user's head (head-mounted display). The virtual image is generated preferably in real time by the control device and depicted on the display unit to make possible an immediate impact of the manipulations conducted by the user and thereby a realistic simulation.

The actuation of a flushing valve can be evaluated for example to display a flushing procedure, by depicting the rise of a liquid level in the visible volume, for example in a region of the lungs or abdomen. If the endoscope lens happens to be below the liquid surface, then the modification of the spatial perception of the cavity and possibly a certain blurring of the image, caused by the refractive index of the liquid, can be shown. Because surgical procedures can result in bleeding that can sharply curtail the endoscopic visibility, bleeding as well can be shown in the simulation; in this case a clear view can be restored by actuation of the flushing valve.

Accordingly, with an actuation of a siphoning valve, a lowering of the liquid level can be displayed. If the user initiates an insufflation, an enlargement of the visible volume can be displayed. Conversely, it can be displayed as a reduction of the volume of the body cavity if the user allows the insufflated gas to escape again or actuates the siphoning valve. With simultaneous insufflation and flushing, the rising of gas bubbles, for example, can also be displayed to achieve as realistic a simulation as possible.

The aforementioned effects that are triggered by the actuation of valves for siphoning, insufflation and flushing, can each be influenced by additional parameters such as the pressure selected on a siphoning, flushing or insufflation pump, or by the type of insufflation gas or flushing liquid. In addition, the movement of the endoscope point, for example, which the user can guide by corresponding control elements, or the orientation of the operating part selected by the user relative to a longitudinal axis of the endoscope can be taken into account in computing the virtual image, for example for displaying the liquid level.

Because the simulation system includes an endoscope apparatus, which comprises at least a line, for example a siphoning line, an insufflation line and/or a flushing line, as well as one or more valves in particular that are to be actuated by the user to affect the at least one line, in addition to means to impact the at least one line with reduced or excess pressure, and means to register pressure and/or pressure flow in the at least one line, a realistic simulation of an endoscopic procedure becomes possible. In particular, it is not necessary thereby to position additional structural elements in the spatially very restricted area of the valves in order to detect the movement of the valve pushbuttons, and the size, structure and weight of the handle of the original endoscope can be taken over unchanged in a training endoscope or can be left unchanged in an adaptation of a clinical usable endoscope. Likewise no additional electric lines from the handle to the control device are required to transmit measured variables of the movement of the valve pushbuttons. Furthermore, according to the invention the actuation of the at least one valve is detected by the actual effect of the valve, namely the impact on the pressure and/or flow conditions in the at least one line on which an effect is exerted, and not only the movement of one or more valve pushbuttons. Finally, in an endoscope in which the insufflation is controlled by the closing of a valve aperture with a finger, the closing of the aperture itself can be detected, and also an incomplete closing of the aperture can be surely recognized and used in the simulation. Hereby too, an especially realistic simulation of the processes in an endoscopic procedure is possible.

Because the actuation of the at least one valve changes both the pressure conditions in a line on which the valve has an impact, and the flow of the particular medium through the line, the actuation of the valve can be detected with the help both of pressure sensors and of flow sensors. Both the measured figures for pressure and those for flow through the line can therefore be used to calculate a virtual image that takes into account the siphoning, insufflation and/or flushing processes controlled by the user. In the process, one or more sensors can each be located on the siphoning, insufflation and/or flushing line, and likewise, simultaneously, pressure and flow sensors can be used on one line, or pressure sensors on one or more lines, and flow sensors on one or more other lines. The use of several sensors, especially of several different sensors, makes possible here an increase in operating security. Thus various measurement principles can be adopted, for example micromechanical silicon sensors integrated as pressure sensors.

According to a preferred embodiment, pressure sensors are used. This has the advantage that no intervention in the flow conditions in the lines is required for measuring, and in particular flow resistance is not used. In addition, pressure sensors are particularly simple in structure and available at reasonable prices. In especially preferred manner, exactly one pressure sensor, which can be of the same structural type, is placed on each of the siphoning, insufflation and flushing lines, making possible an especially simple and cost-effective realization.

Basically both a reduced pressure and an excess pressure in the particular line can serve to detect the actuation of one of the valves. Thus, in one embodiment of the invention the siphoning, insufflation and flushing lines can all be impacted with reduced pressure or all impacted with excess pressure, in particular with an equal pressure. This has the advantage of an especially simple execution, and in particular, identical types of pressure-generating means, such as identical pumps, or else a single pump or a single pressurized container, can be connected to the proximal end areas of the particular lines, so that all three lines are impacted with excess or reduced pressure.

In a preferred embodiment of the invention the pressure-generating means are configured, however, to generate reduced pressure in the siphoning line and to generate excess pressure in the insufflation line and in the flushing line. This has the advantage of an especially realistic simulation, because a possible reaction of the pressure existing in a line on the actuating of the valve thus corresponds to a great extent to reality. Also, in closing the aperture that is connected with the insufflation line with a finger, it can make an appreciable difference for the user whether excess or reduced pressure prevails therein. It is therefore advantageous for a realistic simulation if the insufflation line is provided with excess pressure. In addition, with this choice of pressure conditions, the lines can be configured in similar manner as with an original endoscope, in which the siphoning line is configured for reduced pressure and the flushing and insufflation lines for excess pressure, and the last two lines in addition can be connected with one another in the distal area of the endoscope.

Various types of pressure-generating means can be used to generate the excess or reduced pressure in the lines. Thus, for example, a common pressure reservoir can be connected by a pressure-reduction valve with each of several lines, or one pressure reservoir can be provided for each of the lines. Likewise various types of pumps or compressors can be used to generate the pressure. The pressure-generating means are preferably configured in such a way that the endoscope apparatus, provided it is recognizable for the user, behaves as precisely as possible like a corresponding original endoscope that is connected to the corresponding devices provided for use in endoscopic procedures.

In a preferred embodiment, pumps, in particular roll or diaphragm pumps, are used as pressure-generating means. This has the advantage that the required pressure in each case is available by switching the pump on, and after switching off the pump after a brief period it is disassembled again so that no particular procedures are required for a conversion of the simulation system, for example to retrofit to another training endoscope. In addition, other pressure-generating means such as pressure containers and/or pressure-reduction valves can be provided. Use of roll or diaphragm pumps, in particular those for applications in surgical procedures, has the additional advantage that all adjustments, the gradual pressure build-up on switching on the pump and the other handling in the use of the simulation system correspond to a great extent to reality. This applies particularly for the graduation build-up or reduction of pressure in actuating the valves.

In addition it is advantageous for other pumps to share a common power drive. Thus the pumps can be configured, for example, as roll pumps, each of which comprises a drive shaft on which a common drive engine operates. This permits an independent pressure generation, also for example the generation of reduced pressure in one line and the generation of excess pressure in another line, at especially reasonable cost.

In a preferred embodiment the sensors are analog sensors and the transmission means include an amplifier and an A-D converter. This allows an especially cost-effective realization. The conversion of analog signals of the sensors into digital signals allows the processing by a digital processor, in particular by the processor of the control unit. In addition it is preferred that the digital signals should be transmitted over a USB interface. Such an interface is very widely available and allows in particular the use of a commercially available personal computer to record and process the sensor signals.

It is advantageous, moreover, for the pressure-generating means and the sensor means to be combined in one supply unit. Said unit can include a compact housing that comprises connections for the siphoning line, the insufflation line and the flushing line, and which contains the pressure sensors and pumps for example, and possibly also the pump drives. In addition the supply unit can include electrical and electronic components to transmit measured values of the sensors to the control device, such as amplifiers, A-D converters and an interface for retransmitting data. The supply unit can also contain the control device, resulting in an especially compact realization of the simulation system.

According to an especially preferred embodiment, the endoscope apparatus is connected with the supply unit. This has the advantage of especially simple handling if the simulation system for example is retrofitted into another endoscope apparatus that is modeled on another type of endoscope. For this purpose, in particular, a socket can be available on the supply unit and a plug on the endoscope apparatus that can be inserted into the socket on the supply unit. A configuration that is especially simple to produce is based on using a plug and socket that correspond to the original endoscope's connection to a light source; this connection can also include a connection for a fluid line, for example for the insufflation line. The housing of the supply unit can also correspond to the housing of the light source provided for the particular endoscope. In addition, the supply unit can comprise connections or connecting lines for linking with the proximal area of the siphoning, insufflation or flushing lines of the endoscope apparatus. The supply unit, like the light source, can also comprise a mounting for a flushing bottle, to which the flushing line of the endoscope apparatus is connected and that is connected with the supply unit for pressure impacting. Because this arrangement corresponds to the set-up for clinical use, this has the advantage of an especially realistic simulation.

According to another preferred embodiment, the endoscope apparatus is configured as a flexible endoscope with an operating part, a flexible, elongated shaft and a supply hose and in addition comprises a siphoning connection, a pressure connection linked with the insufflation line, and a flushing connection. Siphoning, pressure and flushing connections can be mounted on the proximal end of the supply hose and can be configured to connect to pressure-generating means, in particular to a connection to a supply unit that includes the pressure-generating means. The flushing connection is configured in particular as a connection of a flushing liquid reservoir. In preferred manner the operating part is configured as a handle, which in particular comprises a siphoning valve with a siphoning valve pushbutton that can be actuated by the user and a flushing valve with a flushing valve pushbutton that can be actuated by the user and that includes an aperture that is connected with the insufflation line and that the user can close with a finger to control the insufflation. The operating part can comprise additional operating elements such as to control the video camera or the distal end area of the endoscope. This configuration makes possible an especially realistic imitation of a clinically usable endoscope.

According to an additional embodiment, the endoscope apparatus is a clinically usable endoscope. Said endoscope comprises the aforementioned connections for linkage to siphoning, insufflation and flushing pumps or to a flushing liquid reservoir, as well as a connection linking to a light source that can also include the connection for the insufflation line. Because of the connection to the supply unit, it is therefore possible to use, as part of the simulation system, a computer that has not been modified, or has been modified only to a minor extent, for this purpose and is suited for clinical service. This results in cost-effective production along with an especially realistic simulation.

With an endoscope that is suited for clinical use, the siphoning line in particular is connected with a valve that in one position opens the line so that air can flow in and in any case a slightly reduced pressure forms that is determined only by the flow resistance in the short proximal-side part of the siphoning line. In operating the siphoning line with reduced pressure, accordingly no substantial excess pressure can develop in the line. In actuating the siphoning valve, this aperture is closed and simultaneously a connection is established to the distal part of the siphoning line of the endoscope. This line, because of its length and small diameter, includes a certain flow resistance so that a measurable reduced or excess pressure can build up in the siphoning line. This pressure is measured and used for recognizing the actuation of the siphoning valve. In similar manner, the flow through the siphoning line depends on the actuation of the valve and in addition or alternatively can be measured for this purpose and used to recognize the actuation of the siphoning valve.

In addition, with an endoscope that is suited for clinical applications, the flushing line is in particular connected with a valve that closes the line in one position so that pressure injected by the pressure-generating means builds up in the flushing line. With the valve in another position, a connection is established to the distal part of the flushing line. As a result, fluid contained in the flushing line can escape; this is preferably air but could also be flushing fluid for the purpose of an especially realistic simulation, especially water, possibly with additives. Because the fluid departs, there is a change in pressure that is measurable and can be used to recognize the actuation of the flushing valve. In analogous manner the flow of the fluid through the flushing line, made possible in this way, can be measured and in addition or alternatively can be measured and used to recognize the actuation of the flushing valve.

With an endoscope suited for clinical applications, the insufflation line is in particular connected with an aperture in the flushing valve that is closed with a finger to inject insufflation gas into a body cavity. While with unclosed aperture a minor pressure difference occurs compared with the ambient pressures and is determined by the flow resistance in the proximal part of the insufflation line, by closing the aperture a clear pressure difference compared to the environment can arise because of the flow resistance in the distal part of the insufflation line and can be used to recognize the closing of the aperture. In analogous manner the corresponding change in the flow through the insufflation line can be measured additionally or alternatively and used to recognize the insufflation.

If the distal apertures in the siphoning line and/or insufflation line can be closed, then the respective difference in pressure or flow can be increased as a result on actuating the respective valve. For this purpose a sealing cap can be placed on the distal end of the endoscope shaft, for example, closing both apertures. This makes possible a secure recognition of the actuation of the respective valve.

Because of the actuations observed in this manner, the corresponding insufflation, siphoning and flushing processes are displayed in the virtual image generated by the control device, so that an endoscope suited for clinical use can be used advantageously within the simulation system.

According to another embodiment the endoscope apparatus is a training endoscope that has been modified for use in the simulation system. This has the advantage that the training endoscope is not required to fulfill the same security requirements as a clinically usable endoscope and is available at reasonable cost.

According to another preferred embodiment of the invention, the sensor means are positioned in the connections of the endoscope. This has the advantage that the endoscope apparatus can be connected in the same manner as an original endoscope with a siphoning pump, an insufflation pump and a flushing pump or a flushing fluid reservoir, so that no modification of the siphoning pump, insufflation pump and flushing pump or of the flushing fluid reservoir is required for the simulation operation. To transmit measured values to the control device, a cable can be provided in this case which is connected to the endoscope apparatus, or else wireless transmission means can be provided.

It is also advantageous if the siphoning line to the distal side of the valve acting on the siphoning line and the insufflation line to the distal side of the valve acting on the insufflation line are closable or closed. In this case upon actuation of the siphoning valve or closing of the aperture of the insufflation line, the flow is made possible or interrupted, so that an especially large flow and pressure modification is produced in the respective line, which makes possible an especially secure recognition of the actuation of the respective valve.

In addition it is advantageous if the siphoning line on the distal side of the operating part is open. The flushing line is thereby opened on actuation of the flushing valve, so that the flow resistance of the remaining distal part of the line ceases. Another result of this is that upon actuation of the valve the pressure or pressure flow in the flushing line is modified by a larger amount, which makes possible an especially secure recognition of the actuation of the respective valve.

An inventive method for training in endoscopic operations includes the following steps:

Provide an endoscope apparatus that comprises an operating part with at least one valve, preferably with a number of valves, and which in addition comprises at least one line, in particular a siphoning line, an insufflation line and/or a flushing line, which are acted on by the at least one valve, Impact the at least one line with reduced or excess pressure, Record an actuation, in particular originated by a user, of the at least one valve by measuring pressure and/or flow in the at least one line, Transmit the measured values for pressure and/or flow to a control unit, Generate a virtual image of an endoscopic operating room setting by the control unit based on the actuation of the valves recorded by the measured values, and Display the virtual image for the user.

The inventive method can include additional steps, such as the recording of the actuation of additional, possibly present operating elements, which for example concern or simulate the activation of a video camera and light source or the bending of the distal end area of the endoscope, and the use of the respective data in generating the virtual image for the user. Likewise, for example, warning signals in case of faulty operations can be generated, for example in exceeding or falling below a pressure and or flow that is suited or physiologically tolerable in the simulated operating room situation, and can be visually or acoustically displayed for the user.

The inventive simulation system and the inventive method have been described for training in endoscopic procedures, and the term "procedures" is intended likewise to include for example diagnostic applications or interventions. Likewise the inventive system as well as the inventive method is suited for demonstration and teaching purposes.

It is assumed that the aforementioned properties, and those yet to be described hereinafter, can be used not only in the combination indicated in each case but also in additional combinations or separately, without departing from the framework of the present invention.

Additional aspects of the invention can be seen from the following description of a preferred embodiment and from the appended drawings.

DETAILED DESCRIPTION OF THE INVENTION

Figure 1:
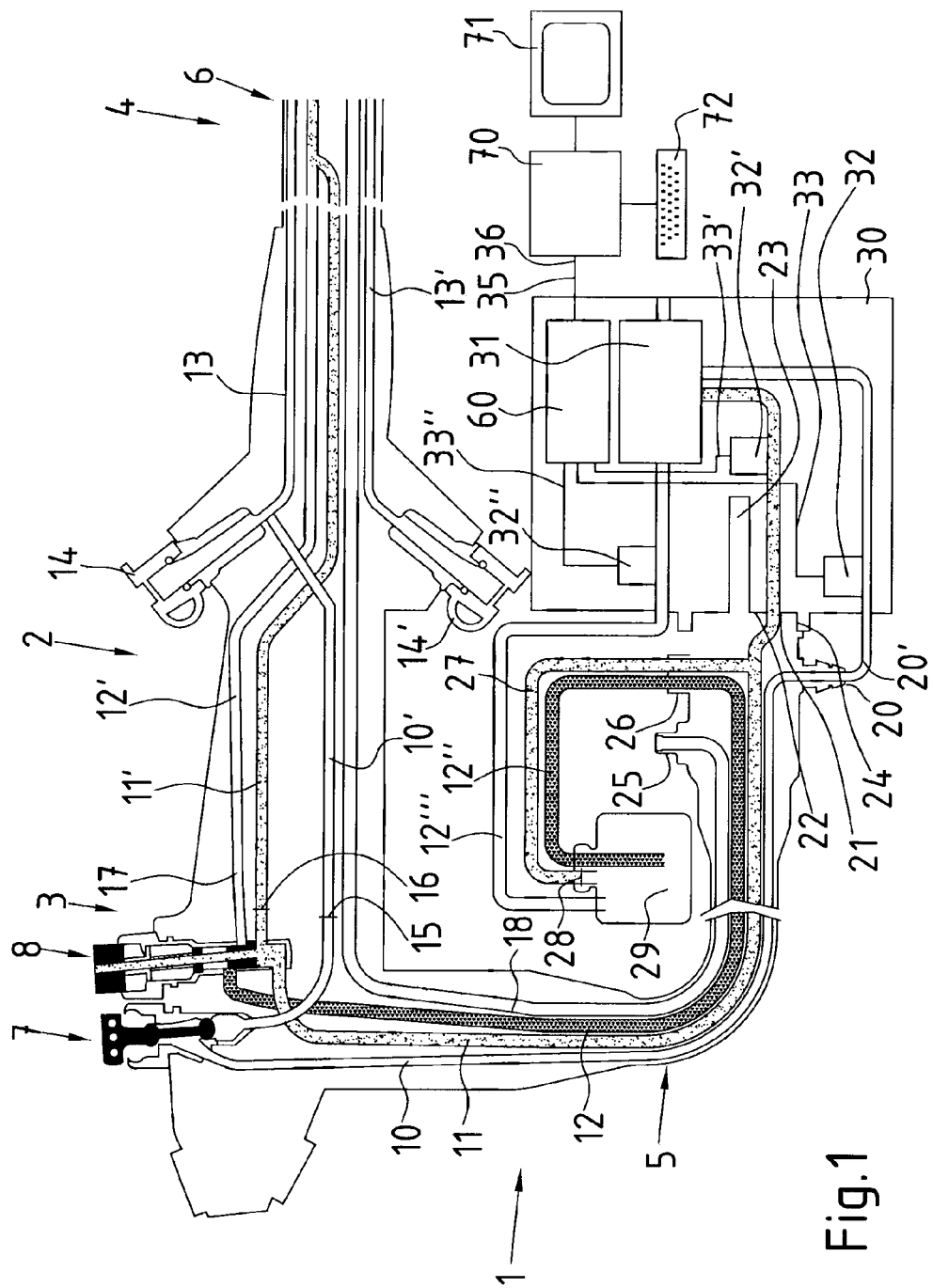
FIG. 1 shows an embodiment of an inventive simulation system in a partly schematic overhead view.

As shown in FIG. 1, an embodiment of the inventive simulation system 1 consists of an endoscope apparatus 2, a supply unit 30, a control unit 70, a display unit 71 as well as additional components in some cases, of which an input device 72 and a flushing fluid reservoir 29, for example, are shown in FIG. 1. The endoscope apparatus 2 includes a handle 3, an elongated flexible shaft 4 provided for insertion into a body cavity, and a supply hose 5. Positioned on the handle 3 are a siphoning valve 7 and a flushing and insufflation valve 8. The endoscope apparatus 2 illustrated in FIG. 1 is configured as a training endoscope, which is the result of modifying an original endoscope suitable for clinical applications.

The siphoning valve 7 serves to control the siphoning from the surgical area. For this purpose, on the proximal side of the siphoning valve 7 in the endoscope apparatus a siphoning line 10 is provided which is acted on by the siphoning valve 7. Likewise, on the distal side of the siphoning valve 7, a siphoning line 10' is provided which in an original endoscope is fed farther through the endoscope shaft 4 all the way to the distal end 6. The siphoning line 10' can lead into an instrument channel 13, which is provided for the insertion of working instruments and can be closed securely with a covering lid 14. The training endoscope illustrated in FIG. 1 is modified from the original endoscope in that the siphoning line 10' on the distal side is closed by a lock 15 so that no flow can occur through the siphoning line 10' on the distal side.

The flushing and insufflation valve 8 serves to control the functions of flushing and insufflation, that is, the introduction of a flushing fluid or of an insufflation gas into the surgical area. An insufflation line 11 and a flushing line 12 which are acted upon by the flushing and insufflation valve 8 are provided for this purpose in the endoscope apparatus, to the proximal side of the flushing and insufflation valve 8. Likewise provided on the distal side of the flushing and insufflation valve 8 is an insufflation line 11', which in an original endoscope is also fed as far as the distal end 6 of the endoscope shaft 4. The insufflation line 11' can lead into the flushing line 12' before the distal end 6. The training endoscope shown in FIG. 1 is further modified from the original endoscope in that the distal-side insufflation line 11' is closed by a lock 16, so that no flow can occur through the distal-side insufflation line 11', and in that the distal-side flushing line 12' comprises an interruption 17 so that a fluid flowing through it can escape there. The leaking of the fluid and a corresponding pressure drop in the distal-side flushing line 12' become possible because the handle 3 is not fluid-tight in configuration; the distal-side flushing line 12' in the area of the handle 3, however, can also be connected with the outer area for this purpose (not illustrated). The siphoning valve 7 and the insufflation and flushing valve 8 have not been modified from an original endoscope.

The endoscope apparatus 2, in addition, can comprise another instrument channel 13', which can be closed by a locking cap 14'. In addition another line 18, which is fed all the way to the distal end 6, can be provided along with other components (not illustrated in FIG. 1) of a clinically usable endoscope in some cases, for example additional operating and transmission elements to control the movement or curvature of the distal end area of the shaft, an illuminating lens, an observation lens, a video camera or a camera dummy with related operating elements.

On the proximal side the endoscope apparatus 2 includes a supply hose 5, through which the lines 10, 11, 12 and 18 run and are each fed in the proximal end area of the supply hose 5 to connections. The siphoning line 10 is connected by the siphoning connection 20 with the supply unit 30, and the connection to the siphoning connection 20 of the endoscope apparatus 2 and possibly to a siphoning connection 20' of the supply unit 30 can be configured detachably. The insufflation line 11 is detachably connected with the supply unit 30 via the pressure connection 21, and the pressure connection 21 is part of a plug 22, which is modeled after the light connection plug of an original endoscope. The plug includes a pin 23, which in the original endoscope serves to couple the illuminating lamp into the illuminating lens of the endoscope. The plug 22 with the pin 23 fits into a socket 24 of the supply unit 30, which is modeled after the light connection socket of the light source for an original endoscope. The additional line 18 is fed to a connection 25, which can be configured as a luer lock.

The flushing line 12 is fed to a flushing connection 26, to which a flushing fluid reservoir 29, for example a flushing fluid bottle, is connected. The flushing connection 26 can likewise correspond to the one in an original endoscope and in addition to the flushing line 12 can include a pressure line 27, which in the area of the proximal end of the supply hose 5 forks off from the insufflation line 11 and in the operation of an original endoscope serves to impact the flushing fluid reservoir 29 with reduced pressure so that the flushing fluid is pressed into this line through the end of the flushing line 12 that is submerged into this line. The partial piece 12" of the flushing line that reaches from the connection 26 to the flushing fluid reservoir 29 and the pressure line 27 can be combined in a hose that contains both lines and is detachably connected with the endoscope apparatus at the connection 26. In operating the inventive simulation system 1 according to the embodiment, the flushing fluid reservoir 29 is preferably empty, that is, filled only with air. The pressure line 27 is closed by a lock 28, and the flushing fluid reservoir 29 is connected with the supply unit 30 by an additional partial piece 12''' of the flushing line.

Inside the supply unit 30, the siphoning line 10, insufflation line 11 and flushing line 12''' are connected with a pump unit 31, which can contain a siphoning pump, an insufflation pump and a flushing pump that are operated by a common power drive (not illustrated). The siphoning pump impacts the siphoning in 10 with reduced pressure, the insufflation pump impacts the insufflation line 11 with excess pressure and the flushing pump the flushing line 12 or 12''' likewise with excess pressure, and here the pressures and conveyed quantities correspond as far as possible to those in the clinical use of an original endoscope with corresponding pumps.

Pressure sensors 32, 32', 32" are mounted on the siphoning line 10, the insufflation line 11 and the flushing line 12''' respectively to measure the pressure in the respective line. The measured values are transmitted in digital or analog form by signal lines 33, 33', 33" to a pre-processing unit 60, from where the pre-processed measured values are transmitted to the control unit 70 via an interface 35 and a cable 36.

The control device 70 includes in particular an image processor to generate or process a video image that is displayed for the user on a display device 71. The video image constitutes as virtual reality an endoscopic view of the body cavity that is subjected to an endoscopic intervention in the training with the simulation system. For this purpose the control unit 70 can in particular include storage means in which data about the particular body cavity are stored and can be called up for the simulation. In addition, associated with the control unit 70 there can be an input unit 72, which is configured for instance as a keyboard or touch-screen and by which the user can define, start and/or control the simulation. The control device 70 can be configured as a PC or else as a special image processor, for example, or can include one of these. In addition, further input and/or display devices can be provided. The inventive simulation system can include still other components, such as a device to detect movements of the distal end 6 or of the shaft 4, which are taken into account in generating the virtual image.

Figure 2:
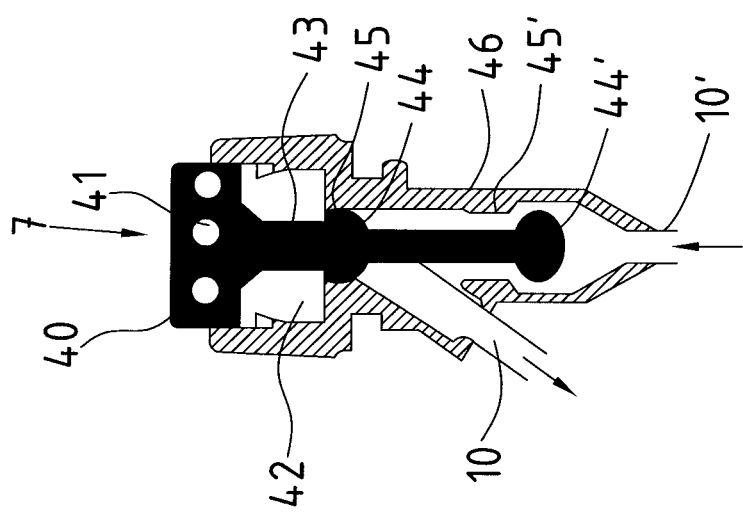
FIG. 2 shows the siphoning valve according to the embodiment in enlarged view in the compressed state.

The siphoning valve 7 includes, as can be seem from FIG. 2, a valve pushbutton 40 that can comprise a number of transverse bores 41 that are connected with an interior space 42 of the valve. In the start-up state, which is shown in FIG. 1, the valve pushbutton 40 stands so far outward that a first shut-off element 44 that is connected with the valve pushbutton 40 by a tappet 43 and is approximately spherical in shape is found above a first valve seat 45 so that the siphoning line 10 is connected with the interior space 42 and from there via the boreholes 41 or also directly via the intermediate space between valve housing 46 and valve pushbutton 40 is connected with the exterior. In this state air can therefore flow unimpeded into the siphoning line 10 when the siphoning line 10 is impacted with reduced pressure. On the other hand, with the siphoning valve 7 in this position, a second, likewise approximately spherical shut-off element 44', which is likewise connected with the valve pushbutton 40 by the tappet 43, is lowered into a second valve seat 45'. No connection exists therefore to the distal-side siphoning line 10'. If, to actuate the siphoning valve 7, the valve pushbutton 40 and thus the tappet 43 is depressed, as shown in FIG. 2, than the first shut-off element 44 also sinks into the first valve seat 45, so that the connection of the siphoning line 10 to the outside is interrupted. On the other hand the second shut-off element 44' raises itself out of the second valve seat 45' so that a connection to the distal siphoning line 10' is established.

Figure 3:
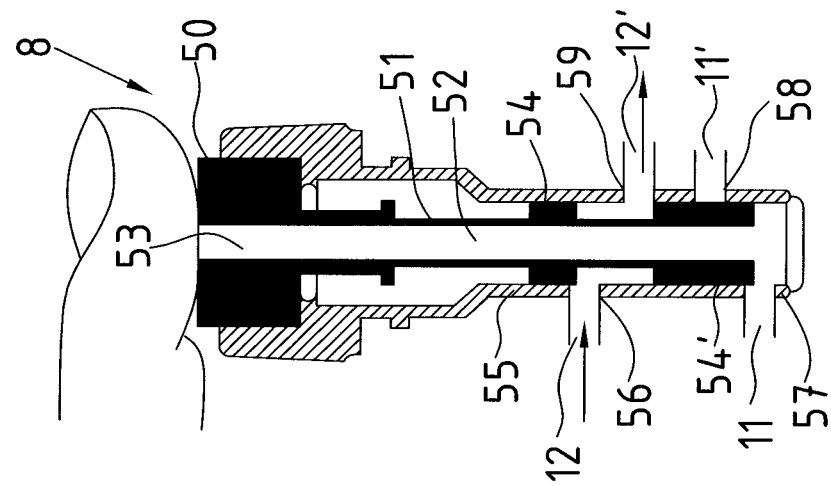
FIG. 3 shows the flushing and insufflation valve according to the embodiment in enlarged view in the compressed state.

The insufflation and flushing valve 8 includes, as can be seen in FIG. 3, a valve pushbutton 50 by which a tappet 51 can be actuated. The valve pushbutton 50 and tappet 51 comprise a central borehole 52 which is connected on one end with the insufflation line 11 and on the other end ends in an aperture 53 into the space outside. Connected with the tappet 51, in the manner of a pump valve, are essentially cylindrical shut-off elements 54, 54', which serve to open and close the proximal-side flushing line 12, distal-side insufflation line 11' and distal-side flushing line 12'. In starting position, as shown in FIG. 1, the valve pushbutton 50 stands so far out that the first shut-off element 54 happens to be above the connection 56 of the flushing line 12 on the valve housing 55, and the second shut-off element 54' closes the connection 59 of the distal-side flushing line 12'. As long as the aperture 53 is not closed, a fluid found in the insufflation line 11 and standing under excess press can escape unimpeded to the outside, so that no significant excess pressure can build up in the insufflation line 11. If the aperture 53 is closed by a finger, as indicated in FIG. 3, on the other hand, pressure can build up in the insufflation line 11. If the insufflation and flushing valve 8 is pressed in by further finger pressure, as shown in FIG. 3, then the connection 58 of the distal-side flushing line 12' is released by the second shut-off element 54' and a fluid located in the proximal-side flushing line 12 can flow into the distal-side flushing line 12'. Because this line is open at the interruption 17, no significant pressure can build up in this valve position in the flushing line 12. The insufflation and flushing valve 8 also allows intermediate positions, which can be reached by depressing the valve pushbutton 50 over a part of the displacement path and which for example make possible a simultaneous partial covering of the connections 58 and 59 of the distal-side insufflation line 11' or flushing line 12'. The first shut-off element can likewise partly cover the connection 56 of the proximal-side flushing line 12.

The arrows shown in FIG. 2 indicate the flow direction of a siphoned-out medium in the siphoning works of an original endoscope, which comprises a siphoning valve of this configuration. The arrows in FIG. 3 each show the flow direction of the flushing medium when it is impacted with excess pressure by the pump unit. The valves 7, 8 can in addition include springs which impact the respective tappet or valve pushbutton with a return force that must be overcome by depressing the valve pushbuttons and that after actuation brings the valve pushbuttons back into their starting position (not illustrated).

Figure 4:
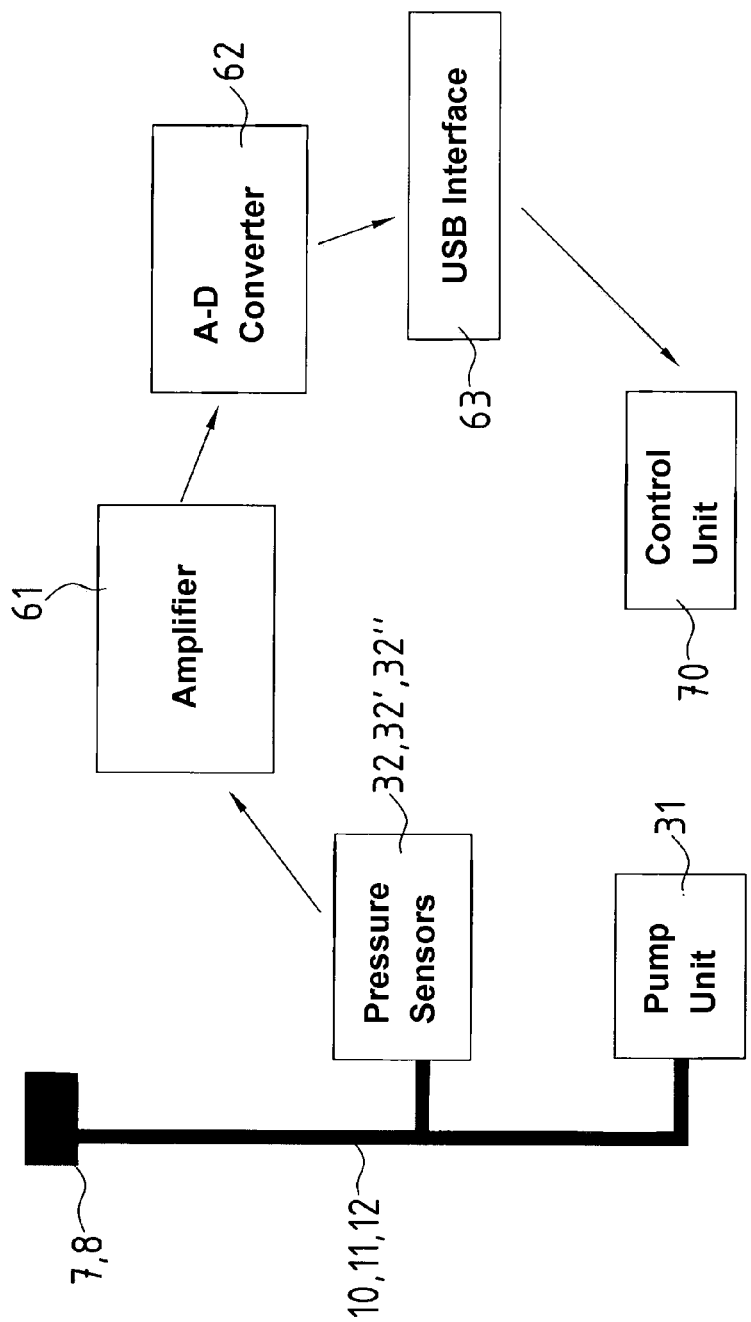
FIG. 4 shows a schematic depiction of the recording and transmission of data of the sensors according to the embodiment.

The data flow from the pressure sensors to the control device 70 is shown in schematic manner by way of example in FIG. 4. On the symbolically depicted siphoning, insufflation or flushing line 10, 11, 12 that leads from the pump unit 31 to the valve 7, 8, a pressure sensor 32, 32', 32" is positioned on a line that branches off from the line 10, 11, 12 and is thereby in fluid communication with the latter, in order to measure the pressure inside the line 10, 11, 12. The pressure values indicated first in analog form are transmitted to an amplifier 61, from there to an A-D converter 62 and from there in digital form to a USB interface 63. From here the transmission proceeds to the control device 70, which can be a PC for example. The amplifier 61, A-D converter 62 and interface 63 can be combined in the pre-processing unit 60.

In performing schooling or training for an endoscopic procedure, the user holds the endoscope apparatus 2 by the handle 3, first without actuating the valves 7, 8. After switching on the pump unit 31, no significant pressure builds up in the siphoning line 10, because with the siphoning valve 7 in the starting position, air can flow into the siphoning line 10. Likewise no significant pressure builds up in the insufflation line 11, because the aperture 53 of the borehole 52 remains open. Only in the flushing line 12, which is closed by the insufflation and flushing valve 8, is there any build-up, corresponding to the adjustment of the pump unit 31 for the flushing function, of excess pressure, which is measured by the sensor 32"; the measured value is transmitted via the signal line 33" to the pre-processing unit 60 and there to the control device 70. Because of the flow resistance in the lines, it is possible also in the siphoning line 10 and in the insufflation line 11 for a minor pressure difference from the outer pressure to arise which can possibly be measurable. The control device 70 determines, on the basis of the pressure in the flushing line 12 and possibly of the low pressure in the flushing line 10 and in the insufflation line 11, that the valves 7 and 8 are in start-up position, that is, that none of the siphoning, insufflation or flushing functions have been actuated by the user. This is correspondingly taken into account in computing the virtual image.

To start the insufflation, the user covers the aperture 53 with a finger. Now an excess pressure can be built up in the insufflation line 11, corresponding to the setting of the pump unit 31 for the insufflation. This excess pressure is measured by the sensor 32'. On the basis of the transmitted pressure value of the sensor 32', the control device determines that the user has initiated the insufflation, as was taken into account in generating the virtual image. Flow resistances, volumes and settings are preferably selected in such a way that the pressure build-up occurs in similar manner, possibly gradually, as with an original endoscope in the corresponding operation situation.

If the user now presses the insufflation and flushing valve 8 downward, nothing changes with the pressure in the insufflation line 11 because the distal-side insufflation line is closed in any case by the lock 16. On the other hand, a connection is now established between the proximal-side flushing line 12 and the distal-side flushing line 12', where the fluid contained in the flushing line 12 can escape because of the interruption 17. Pressure built up in the flushing line 12 or 12" is therefore returned to zero or to a very low value determined by the flow resistance. Hereby, too, the flow resistances, volumes and settings are selected in such a way that the timeline of the pressure reduction occurs in realistic manner. The control device 70 ascertains from the pressure drop in the flushing line 12" that the flushing process has been triggered, as is taken into account in calculating the virtual image.

Depending on the simulated operation or assignment, it is also possible of course to select a sequence other than the one described by way of example above.

The invention claimed is:

1. A simulation system for training in endoscopic procedures, including:
   an endoscope apparatus that comprises an operating handle with at least one valve, and at least one line upon which the at least one valve acts, the at least one line transmitting fluid;
   a pressure-generating device to impact the at least one line with reduced or excess pressure;
   a sensor disposed in a supply unit that is connected to the endoscope apparatus, the sensor measuring pressure or flow in the at least one line;
   a control device to generate a virtual image of an endoscopic operating scene depending on an actuation of the at least one valve via measuring at least one of pressure or flow in the at least one line;
   transmission means to transmit measured values provided by the sensor to the control device to be used in determining the actuation of the at least one valve and generating the virtual image; and
   a display device to display the virtual image.

2. The simulation system according to claim 1, wherein the operating handle comprises a number of valves and the endoscope apparatus comprises a siphoning line, an insufflation line and a flushing line upon which the valves act.

3. The simulation system according to claim 1, wherein the sensor comprises one or more pressure sensors.

4. The simulation system according to claim 2, wherein the pressure-generating device is configured to generate reduced pressure in the siphoning line and to generate excess pressure in the insufflation line and in the flushing line.

5. The simulation system according to claim 1, wherein the pressure-generating device comprises one or more pumps.

6. The simulation system according to claim 1, wherein the sensor includes analog sensors and the transmission means include an amplifier, an A-D converter and a USB interface.

7. The simulation system according to claim 1, wherein the pressure-generating device and the sensor are combined in the supply unit.

8. The simulation system according to claim 7, wherein the endoscope apparatus is detachably connected with the supply unit.

9. The simulation system according to claim 1, wherein the endoscope apparatus is a flexible endoscope with a flexible, elongated shaft and a supply hose and comprises a siphoning connection, a pressure connection and a flushing connection.

10. The simulation system according to claim 1, wherein the endoscope apparatus is an endoscope suited for clinical use.

11. The simulation system according to claim 1, wherein the endoscope apparatus is a training endoscope.

12. The simulation system according to claim 9, wherein the sensor comprises multiple sensors, said sensors being positioned in the siphoning, pressure, and flushing connections of the endoscope apparatus.

13. The simulation system according to claim 2, wherein the siphoning line to the distal side of the valve that acts on the siphoning line and the insufflation line to the distal side of the valve that acts on the insufflation line can be closed.

14. The simulation system according to claim 2, wherein the siphoning line to the distal side of the valve that acts on the siphoning line and the insufflation line to the distal side of the valve that works on the insufflation line are closed and the flushing line to the distal side of the valve that acts on the flushing line is open.

15. A method for training in endoscopic procedures, including the following steps:
provide an endoscope apparatus, which comprises an operating part with at least one valve and at least one line upon which the at least one valve acts,
connect a supply unit with the endoscope apparatus, the supply unit having at least one sensor for measuring at least one of pressure or flow;
impact the at least one line with reduced or excess pressure using a pressure-generating device,
detect an actuation of the at least one valve by measuring pressure or flow in the at least one line using the at least one sensor in the supply unit,
transmit values measured by the at least one sensor to a control device,
generate a virtual image of an endoscopic operating scene by the control device depending on the actuation of the valves recorded by the measured values and
display the virtual image for a user.

16. The simulation system according to claim 2, wherein the sensor comprises one or more pressure sensors.

17. The simulation system according to claim 3, wherein the pressure-generating device is configured to generate reduced pressure in a siphoning line of the endoscope apparatus and to generate excess pressure in an insufflation line and a flushing line of the endoscope apparatus.

18. The simulation system according to claim 10, wherein the sensor comprises multiple sensors, said sensors being positioned in siphoning, pressure, and flushing connections of the endoscope.

19. The simulation system according to claim 11, wherein the sensor comprises multiple sensors, said sensors being positioned in siphoning, pressure, and flushing connections of the endoscope.

* * * * *